United States Patent [19]

Miller et al.

[11] Patent Number: 5,271,947
[45] Date of Patent: Dec. 21, 1993

[54] METHOD FOR CONTROLLING DUST MITES

[76] Inventors: Annette Miller; Jeffrey D. Miller, both of 28 High Ridge Ave., Ridgefield, Conn. 06877

[21] Appl. No.: 735,063

[22] Filed: Jul. 24, 1991

[51] Int. Cl.$^5$ .............................................. A01N 59/08
[52] U.S. Cl. .................................... 424/680; 424/677; 424/678; 424/679; 424/715
[58] Field of Search ................................ 424/680, 677

[56] References Cited

U.S. PATENT DOCUMENTS

68,867  9/1867  Galbraith ............................ 424/680

FOREIGN PATENT DOCUMENTS

1031010  2/1989  China .
1048484  1/1991  China .
 678044  3/1930  France .
 886667  10/1943  France .

OTHER PUBLICATIONS

Arlian et al. "The prevalence of houst dust mites, Dermatophagoides spp, and associated environmental conditions in homes in Ohio." J. Allergy Clin. Immunol. Jun. 1982, pp. 527-532.
McDonald et al. "The role of water temperature and laundry procedures in reducing house dust mite populations and allergen content of bedding." J. Allergy Clin. Immunol. Oct. 1992, pp. 599-608.
Osman et al. "Versuche Zur Reduzierung der Population von Tetranychus arabicus . . . ". Anz. Schaedlingskde., Pflanzenschutz, 49, pp. 42-44 (1976).
Websters New World Dictionary, Third College Edition, N.Y., Simon & Schuster, Inc., 1988, pp. 7 and 869.
Chemical Abstracts 113: 54368w Aug. 13, 1990.
Voorhorst et al, The Journal of Allergy, vol. 39, No. 6, pp. 325-339 (Jun. 1967).
Platts-Mills et al, The Journal of Allergy and Clinical Immunology, vol. 80, No. 6, pp. 755-775 (Dec. 1987).
Arlian, Immunology and Allergy Clinics of North America, vol. 9, No. 2, pp. 339-356 (Aug. 1989).
Tovey et al, Nature, vol. 289, p. 592 (Feb. 1981).
Sporik et al, The New England Journal of Medicine, vol. 323, No. 8, pp. 502-507 (Aug. 1990).
Boner et al, Annals of Allergy, vol. 54, pp. 42-45 (Jan. 1985).
Platts-Mills et al, The Lancet, pp. 675-677 (Sep. 1982).
Lang et al, Environmental Entomology, vol. 6, No. 5, pp. 643-648 (Oct. 1977).
Murray et al, Pediatrics, vol. 71, No. 3, pp. 418-422 (Mar. 1983).
Walshaw et al, Quarterly Journal of Medicine, vol. 58, No. 226, pp. 199-215 (Feb. 1986).
Sly et al, Annals of Allergy, vol. 54, pp. 209-212 (Mar. 1985).
Burr et al, Thorax, vol. 35, pp. 506-512 (1980).
Collof, 1(2), pp. 3-8, (1990) Pesticide Outlook 1(2).
The Journal of Allergy and Clinical Immunology, vol. 83, No. 2, Pt. 1, pp. 416-427 (Feb. 1989).
Samet, Am Rev Respir Dis, No. 142, pp. 915-917 (1990).

Primary Examiner—Allen J. Robinson
Assistant Examiner—John D. Pak
Attorney, Agent, or Firm—Rodman & Rodman

[57] ABSTRACT

A method for reducing the proliferation of dust mites in substrates inhabited by dust mites is accomplished by contacting the substrates such as bedding materials, rugs and upholstered furniture with a sufficient amount of finely divided salt which functions as an acaricide against dust mites, thereby killing the dust mites.

6 Claims, No Drawings

METHOD FOR CONTROLLING DUST MITES

BACKGROUND OF THE INVENTION

1. Field of the Invention

This invention relates to a method for reducing the population of dust mites by contacting salt crystals on substrates inhabited by dust mites.

2. Background of the Invention

It has been known for many years that common house dust is an important cause of asthma, rhinitis and eczema in allergic individuals. The mite *Dermatophygoides pteronyssinus* has been identified as a major source of house dust allergen. This mite and the related mites *D. farinae, D. microceras* and *Euroglyphus maynei* are the predominant house dust mites in temperate climates in countries including the United States and Europe.

Dust Mites are not insects, but are eight-legged arachnids, relatives of ticks and spiders. They live in close association with humans (or other mammals), their main food source being the shed scales from skin. Adult mites are approximately 300 microns (3/10 mm) in size, having developed over approximately 25 days through egg, larval and nymph stages. Adults live for 2 to 3½ months, during which time each female can produce about 20-40 eggs. Dust mites are photophobic, living deep in pillows, mattresses, carpets, upholstered furniture and other soft materials.

In addition to a food source, the other essential requirement for dust mite growth is adequate humidity. Dust mites are 75% water by weight. They do not drink water, but must absorb water vapor from the air in order to survive. Specialized glands above their first pair of legs produce secretions high in sodium and potassium chloride, which act to absorb water vapor from surrounding air. This can only be accomplished if the surrounding humidity is sufficiently high. Relative humidities of about 70-75% are optimal for dust mite growth. Dust mites will die at humidities of 50% or less. In geographical areas where humidity is high, dust mites are present in nearly all homes and may be as plentiful as 18,000 mites per gram of dust. Literally millions of mites can inhibit a single bed or carpet.

About ten years ago, it was demonstrated that a major dust mite allergen was present in mite fecal particles. Each mite produces about 20 fecal particles per day, and more than 100,000 of them may be present in a gram of dust. These fecal particles vary from about 10 to 40 microns in size, comparable to the size of pollen grains, and become airborne during domestic activity such as making beds and vacuuming carpets. The chemical structure of mite allergens has been defined, including that of other allergens which are present both on mite bodies and fecal particles.

Acute exposure to mite allergens has been shown to provoke wheezing, rhinitis, eustacian tube obstruction or eczema in sensitized patients. Chronic exposure can cause bronchial hyper-reactivity and chronic asthma. There is a correlation between the level of exposure to house dust mite allergen in early childhood and the likelihood of the subsequent development of asthma. Conversely, asthmatics sensitive to dust mites improve in environments without mites, such as at high altitudes or in hospital rooms. Attempts have therefore been made to decrease patients' exposure to dust mites in the home.

Studies of dust avoidance measures in homes have shown that the use of impermeable mattress and pillow encasings and the removal of bedroom carpeting are associated with a decrease in mite counts. These measures have also been shown to be of clinical value, with a decrease in symptoms and medication requirements occurring in children and adults with dust-sensitive asthma when pillows and mattresses are encased and carpets are removed.

Although carpets and upholstered furniture are major sites of dust mite growth, many allergic individuals are unable or unwilling to remove these from their home. Vacuuming does not remove dust mites or significantly decrease dust mite allergen levels, and in fact, vacuuming of carpets actually increases the amount of airborne dust. It is thus not surprising that trials employing vacuuming rather than removal of carpets failed to produce clinical improvement.

Because of the importance of carpets and textile materials as habitats of dust mites, various chemical acaricides have been proposed to kill mites in those locations.

U.S. Pat. No. 4,666,940 to Bischoff et al discloses an acaricidal composition whose active ingredient is benzyl benzoate. The acaricidal substance is said to be applicable in the form of a liquid, a foam, or as a semi-aqueous pulverulent cleanser. The particle sizes of the residue after application and drying range from about 2 to 100 microns, which is said to be a suitable size range for oral ingestion by dust mites.

Other chemical agents which have been used to kill dust mites include primiphos methyl, natamycin, bioallethrin, deltamethrin and methoprene. These organic compounds may be expensive, and many of them have caused skin, eye or bronchial irritation. They also have the potential to cause allergic or other adverse reactions. The use of such organic compounds in households is therefore not the ideal solution to the problem of reducing the population of dust mites. Liquid nitrogen has been used to kill dust mites in carpets by freezing, but use of liquid nitrogen is potentially dangerous and it must therefore be applied only by a trained technician. An alternative approach is the use of tannic acid, which denatures dust mite antigen but which does not kill the dust mites themselves.

U.S. Pat. No. 3,973,011 to Bohner et al discloses organic oxadiazolyl compounds which are said to be effective pesticides against animal and plant pests. The oxadiazolyl compounds can be used alone or in combination with dispersants, such as alkali salts.

U.S. Pat. No. 1,767,528 to Jones discloses a cleaning and disinfecting compound designed for household use, which contains common salt. U.S. Pat. Nos. 1,576,105 and 1,576,106 both to Fetherston disclose the use of sodium chloride for controlling the proliferation of microbes in garbage containers to reduce odors and other problems associated with decomposing garbage.

U.S. Pat. No. 2,299,604 to Weirich relates to antimycotics containing sodium chloride for controlling athlete's foot. U.S. Pat. No. 191,476 to Seligman discloses a compound for disinfecting and deodorizing horse stables, which contains mineral salts such as potassium carbonate or potassium hydroxide.

U.S. Pat. No. 088,300 to Jaycox discloses a flea powder which includes 25% abstract of Mentha pulegium (a plant commonly known as pennyroyal), 30% snuff, 20% Sinapis (a mustard) and 25% salt. The components are ground individually then uniformly mixed into a powder. Jaycox discloses that the degree of fineness of the ground components is immaterial in using the composition to destroy fleas.

It should be noted that dust mites are as far removed from fleas, as human beings are from turtles.

To be effective in reducing the population of dust mites, acaricidal compounds should be contacted on various substrates which accumulate mites, such as carpets, rugs, bedding materials, such as mattresses, blankets, bedspreads and pillows, upholstered furnishings and toys made from various fabrics, especially stuffed animals. Obviously, the acaricidal substances must not be allergens or irritants to persons coming into close proximity with such substrates, and who are allergic to house dust.

The present invention uses common salt or its substitutes as inexpensive, environmentally safe acaricides.

SUMMARY OF THE INVENTION

The present invention is based upon the discovery that contacting substrates inhabited by dust mites with salt crystals as the active ingredient, kills and inhibits the proliferation of dust mites.

DESCRIPTION OF THE PREFERRED EMBODIMENTS

In accordance with the present invention, it has been found that contacting finely divided salt crystals on substrates inhabited by dust mites significantly reduces the number of live larval, nymph and adult dust mites. The salt crystals have been found to act as an acaricide to kill the dust mites.

In treating the substrates inhabited by dust mites, the objective is to infiltrate the substrate environment with an acaricidally effective amount of salt.

The size of the salt crystals should be such that they adhere to all areas of carpet or textile where the mites are present. The size must also be such as to efficiently produce an acaricidal effect by placing a maximum number of salt crystals in proximity to a maximum number of dust mites.

Sodium chloride is readily available in granular, crystal and powdered forms. Granular sodium chloride consists of small pellets of salt. Crystal sodium chloride has the consistency of ordinary table salt, while powdered sodium chloride has the consistency of talcum powder.

Although the mechanism of action of salt as an acaricide is uncertain, it is theorized that the dust mites, which are very susceptible to dehydration, are being affected by the change in osmotic pressure induced by the salt, with subsequent water loss from the dust mite resulting in its death.

Other hygroscopic salts which can be used include potassium chloride, calcium chloride, sodium carbonate, ferric sulfate and potassium thiosulfate. The salt can be applied to the carpet or other textile or soft material substrate in finely divided form as 100% salt. Alternatively, the salt can be mixed with other active or inactive materials.

The salt is applied in amounts sufficient to kill dust mites, which can be accomplished by evenly distributing the appropriate amount of salt over the substrate material and then contacting it throughout the substrate material, with such suitable means as a broom or brush so that it thoroughly infiltrates the substrate material. The salt is left to remain in place for about 1 to 2 weeks. It is then suitably removed by vacuuming. Salt applications can be repeated at intervals of about 2 weeks to 12 months, preferably about 1 to 6 months and most preferably about 2 to 4 months, depending on local conditions and the degree of mite infestation.

A suitable amount of salt for substrates such as carpets and rugs can vary from about 1 to 1,000 grams, preferably about 10 to 500 grams and most preferably about 50 to 200 grams per square meter. Naturally, greater or lesser amounts of salt can be used, depending upon the extent of dust mite infestation. Beyond a certain point, an excessive amount of salt will not achieve a corresponding degree in the reduction of dust mite population in the substrate. It has been found that about 100 grams of finely divided salt per square meter of substrate is generally sufficient to kill a significant amount of dust mites on the order of about 90 to 99%.

The following examples illustrate specific embodiments of the present invention. All parts and percentages are by weight unless otherwise noted.

EXAMPLE 1

Dust mites of the species D.pteronyssinus were grown in culture on TetraMin ® brand fish food (Tetrawerke GmbH) at 75° F. and 75% relative humidity for two to three months to establish a sufficient population. Approximately 1 teaspoon of cultured mites and food were then rubbed into sections of carpet measuring 325 square centimeters. Carpets were used in various size tufts from ¼ inch to ¾ inch. These carpet sections were then incubated under the same conditions for an additional three weeks.

Seven sections of mite infested carpet were studied. Each section was cut in half. One half was treated with sodium chloride powder which was sprinkled on evenly and brushed in in amounts of 12.5 milligrams per square centimeter. The other half was left untreated as a control. Both halves of each section were then returned to the 75° F. and 75% relative humidity conditions for an additional two weeks.

At the end of two weeks, the mites in each section of carpet were counted by the "heat escape method." A sheet of clear adhesive faced plastic (Contact ® brand self-adhesive covering, Rubbermaid Inc.) was placed adhesive side down on each section of carpet, and covered with opaque glass and a three pound weight. The thus prepared carpet was then placed upright on a hot plate (Fisher Scientific #11-498-7H). Using a surface thermometer, the temperature of the hot plate was increased by about 1° C. per minute, from an ambient temperature of 24° C. to a temperature of 70° C. over a period of approximately 45 minutes. The temperature was maintained at 70° C. for an additional 15 minutes. In an attempt to escape from the heat, the mites moved from their usual habitat deep in the carpet to its surface, where they became stuck to the adhesive covering.

The adhesive sheet was then removed and overlayed upon a clear plastic grid. The sheet and grid were examined under a stereomicroscope, and the numbers of immature and adult mites in the center 25 square centimeters of each sample were counted. Table 1, which follows, shows the number of living mites in each treated and untreated section of carpet.

TABLE 1

| Sample No. | Number of Dust Mites | |
|---|---|---|
| | Untreated control | Sodium chloride powder treated |
| 1 | 1073 | 29 |
| 2 | 612 | 11 |
| 3 | 472 | 27 |

TABLE 1-continued

| | Number of Dust Mites | |
|---|---|---|
| Sample No. | Untreated control | Sodium chloride powder treated |
| 4 | 561 | 62 |
| 5 | 1025 | 6 |
| 6 | 2568 | 15 |
| 7 | 683 | 80 |
| Mean: | 999.1 | 32.8 |

The mean mite count in 25 square centimeter of the untreated halves of the carpet section was 999.1; the mean count in the treated halves was 32.8. These differences analyzed with a paired t-test were statistically significant at a p value of <0.01. The mite counts were decreased on average by more than by 95%.

EXAMPLE 2

To compare the effects of salt having different particle sizes, 3 pieces of carpet, each approximately 500 square centimeters were labeled Samples A, B and C, respectively. Each sample was inoculated with cultures of *D. pteronyssinus* mites and incubated for three weeks, as described in Example 1. Each carpet sample was then cut into three equal sections. One section of each sample was treated with powdered sodium chloride having the consistency of talcum powder. The second section of each sample was treated with crystal salt having the consistency of ordinary table salt. The third section of each sample was left as an untreated control. The amount of salt added was 12.5 milligrams per square centimeter, the same as in Example 1. After two weeks, the heat escape method detailed in Example 1 was performed and the number of mites per 25 square centimeter area were counted and tabulated in Table 2, which follows:

TABLE 2

| | Number of Mites | | |
|---|---|---|---|
| Sample No. | Untreated control | Crystal salt | Powdered salt |
| A | 320 | 232 | 71 |
| B | 383 | 101 | 22 |
| C | 135 | 192 | 11 |
| Mean: | 279 | 142 | 35 |

It can be seen that although crystal salt produced a decrease in the number of mites in two of the three samples, it was not as effective as the powdered salt, which decreased the number of mites significantly in all three samples. This indicates that the smaller more finely divided salt particles in powdered salt are a more effective acaricide in such substrates.

What is claimed is:

1. A method for reducing the population of dust mites selected from the group consisting of *Dermatophagoides pteronyssinus, Dermatophagoides farinae, Dermatophagoides microceras* and *Euroglyphus maynei* living in a substrate in a household environment, consisting essentially of contacting the substrate in a household environment populated by said mites with a miticidally effective amount of sodium chloride powder, having the consistency of talcum powder, thereby reducing the population of said mites.

2. The method of claim 1, wherein the sodium chloride powder is contacted to said substrate in concentrations of about 1 to 1000 grams per square meter.

3. The method of claim 1, wherein the substrate is selected from the group consisting of carpets, rugs, bedding materials, upholstered furnishings and toys made from fabrics.

4. The method of claim 1, wherein the application of sodium chloride powder is repeated at intervals of about two weeks to 12 months.

5. The method of claim 3, wherein the bedding materials are selected from the group consisting of pillows, mattresses, blankets and bedspreads.

6. The method of claim 1, conducted at a relative humidity of about 50% or higher.

* * * * *